(12) United States Patent
Dershem

(10) Patent No.: US 8,398,898 B2
(45) Date of Patent: Mar. 19, 2013

(54) SOLUBLE METAL SALTS FOR USE AS CONDUCTIVITY PROMOTERS

(75) Inventor: Stephen M Dershem, San Diego, CA (US)

(73) Assignee: Designer Molecules, Inc., San Diego, CA (US)

( * ) Notice: Subject to any disclaimer, the term of this patent is extended or adjusted under 35 U.S.C. 154(b) by 900 days.

(21) Appl. No.: 12/391,204

(22) Filed: Feb. 23, 2009

(65) Prior Publication Data

US 2009/0215940 A1    Aug. 27, 2009

Related U.S. Application Data

(60) Provisional application No. 61/030,948, filed on Feb. 23, 2008.

(51) Int. Cl.
   *H01B 1/02*    (2006.01)
(52) U.S. Cl. .................. 252/520.3; 252/514; 252/518.1; 524/403; 525/248; 525/262
(58) Field of Classification Search .................. 252/513, 252/514, 518.1, 520.3; 524/403; 525/248, 525/262
   See application file for complete search history.

(56) References Cited

U.S. PATENT DOCUMENTS

| | | | |
|---|---|---|---|
| 4,483,898 A | 11/1984 | Schonhorn et al. |
| 4,658,049 A | 4/1987 | Nakano et al. |
| 4,968,738 A | 11/1990 | Dershem |
| 5,045,127 A | 9/1991 | Dershem et al. |
| 5,064,480 A | 11/1991 | Dershem et al. |
| 5,232,962 A | 8/1993 | Dershem et al. |
| 5,306,333 A | 4/1994 | Dershem et al. |
| 5,358,992 A | 10/1994 | Dershem et al. |
| 5,403,389 A | 4/1995 | Dershem |
| 5,447,988 A | 9/1995 | Dershem et al. |
| 5,489,641 A | 2/1996 | Dershem |
| 5,646,241 A | 7/1997 | Dershem et al. |
| 5,714,086 A | 2/1998 | Osuna et al. |
| 5,717,034 A | 2/1998 | Dershem et al. |
| 5,718,941 A | 2/1998 | Dershem et al. |
| 5,753,748 A | 5/1998 | Dershem et al. |
| 5,861,111 A | 1/1999 | Dershem et al. |
| 5,969,036 A | 10/1999 | Dershem |
| 5,973,166 A | 10/1999 | Mizori et al. |
| 6,034,194 A | 3/2000 | Dershem |
| 6,034,195 A | 3/2000 | Dershem |
| 6,036,889 A | 3/2000 | Kydd |
| 6,121,358 A | 9/2000 | Dershem et al. |
| 6,187,886 B1 | 2/2001 | Husson et al. |
| 6,211,320 B1 | 4/2001 | Dershem et al. |
| 6,379,745 B1 | 4/2002 | Kydd |
| 6,423,780 B1 | 7/2002 | Dershem et al. |
| 6,429,281 B1 | 8/2002 | Dershem et al. |
| 6,521,731 B2 | 2/2003 | Dershem et al. |
| 6,620,946 B2 | 9/2003 | Dershem et al. |
| 6,743,852 B2 | 6/2004 | Dershem et al. |
| 6,750,301 B1 | 6/2004 | Bonneau et al. |
| 6,790,597 B2 | 9/2004 | Dershem |
| 6,825,245 B2 | 11/2004 | Dershem |
| 6,831,132 B2 | 12/2004 | Liu et al. |
| 6,852,814 B2 | 2/2005 | Dershem et al. |
| 6,916,856 B2 | 7/2005 | Dershem |
| 6,946,523 B2 | 9/2005 | Dershem et al. |
| 6,960,636 B2 | 11/2005 | Dershem et al. |
| 6,963,001 B2 | 11/2005 | Dershem et al. |
| 7,102,015 B2 | 9/2006 | Dershem et al. |
| 7,115,218 B2 | 10/2006 | Kydd |
| 7,157,587 B2 | 1/2007 | Mizori et al. |
| 7,176,044 B2 | 2/2007 | Forray et al. |
| 7,199,249 B2 | 4/2007 | Liu et al. |
| 7,208,566 B2 | 4/2007 | Mizori et al. |
| 7,285,613 B2 | 10/2007 | Dershem et al. |
| 7,309,724 B2 | 12/2007 | Dershem et al. |
| 7,517,925 B2 | 4/2009 | Dershem et al. |
| 7,678,879 B2 | 3/2010 | Dershem |
| 2002/0062923 A1 | 5/2002 | Forray |
| 2002/0099168 A1 | 7/2002 | Dershem et al. |
| 2002/0188137 A1 | 12/2002 | Dershem et al. |
| 2002/0193541 A1 | 12/2002 | Dershem et al. |
| 2002/0198356 A1 | 12/2002 | Dershem et al. |
| 2003/0008992 A1 | 1/2003 | Dershem et al. |
| 2003/0055121 A1 | 3/2003 | Dershem et al. |
| 2003/0060531 A1 | 3/2003 | Dershem et al. |
| 2003/0087999 A1 | 5/2003 | Dershem et al. |
| 2003/0109666 A1 | 6/2003 | Dershem et al. |
| 2003/0125551 A1 | 7/2003 | Dershem et al. |
| 2003/0199638 A1 | 10/2003 | Liu et al. |
| 2003/0208016 A1 | 11/2003 | Dershem et al. |
| 2004/0006166 A1 | 1/2004 | Liu et al. |
| 2004/0019224 A1 | 1/2004 | Dershem et al. |
| 2004/0077798 A1 | 4/2004 | Dershem et al. |

(Continued)

FOREIGN PATENT DOCUMENTS

| | | |
|---|---|---|
| JP | 11246759 | 9/1999 |
| WO | WO2004099331 | 11/2004 |
| WO | WO-2005121190 | 12/2005 |
| WO | WO-2007100329 | 9/2007 |
| WO | WO-2008077141 | 6/2008 |
| WO | WO-2008124797 | 10/2008 |
| WO | WO-2008130894 | 10/2008 |
| WO | WO-2010019832 | 2/2010 |

OTHER PUBLICATIONS

Ganapathy et al., "Ring-opening polymerization of-lactide in supercritical carbon dioxide using PDMS based stabilizers", *European Polymer Journal 43*: Jan. 2007, 119-126. Lim et al., "Synthesis and characterization of Poly (dimethyl siloxane)-Poly[alkyl (meth)acrylic acid] Block Copolymers", *Macromolecules 32*: 1992, 2811-2815.

Southward, "Surface Conductive and Reflective Silver-Polyimide Composite Films Prepared Via Thermally Induced Reduction of(1,1,1-Trifluoro-2,4-Pentanedionato)Silver(1) in a Curing Poly(Amic Acid) Matrix", *Polymer Preprints*, 39, 1 1998, 423-424.

*Primary Examiner* — Mark Kopec
*Assistant Examiner* — Haidung Nguyen
(74) *Attorney, Agent, or Firm* — The Law Office of Jane K. Babin, Proffesional Corporation; Jane K. Babin

(57) ABSTRACT

The present invention provides conductivity promoters, and in particular soluble conductivity promoters that contain a hydrocarbon moiety or a siloxane moiety and a metal. The present invention also provides methods of making soluble conductivity promoters and adhesive compositions containing the conductivity promoters of the invention.

17 Claims, 3 Drawing Sheets

U.S. PATENT DOCUMENTS

| | | | |
|---|---|---|---|
| 2004/0082724 A1 | 4/2004 | Dershem et al. | |
| 2004/0102566 A1 | 5/2004 | Forray et al. | |
| 2004/0123948 A1 | 7/2004 | Dershem et al. | |
| 2004/0225026 A1 | 11/2004 | Mizori et al. | |
| 2004/0225045 A1 | 11/2004 | Forray | |
| 2004/0225059 A1 | 11/2004 | Mizori et al. | |
| 2005/0107542 A1 | 5/2005 | Liu et al. | |
| 2005/0136620 A1 | 6/2005 | Dershem et al. | |
| 2005/0137277 A1 | 6/2005 | Dershem et al. | |
| 2005/0267254 A1 | 12/2005 | Mizori et al. | |
| 2005/0272888 A1 | 12/2005 | Dershem et al. | |
| 2006/0009578 A1 | 1/2006 | Dershem | |
| 2006/0063014 A1 | 3/2006 | Forray | |
| 2006/0069232 A1 | 3/2006 | Dershem | |
| 2006/0142517 A1 | 6/2006 | Dershem | |
| 2006/0284141 A1 * | 12/2006 | Musa | 252/500 |
| 2007/0155869 A1 | 7/2007 | Dershem et al. | |
| 2007/0205399 A1 | 9/2007 | Mizori | |
| 2007/0299154 A1 | 12/2007 | Dershem et al. | |
| 2008/0017308 A1 | 1/2008 | Dershem et al. | |
| 2008/0075961 A1 | 3/2008 | Mizori | |
| 2008/0075963 A1 | 3/2008 | Dershem | |
| 2008/0075965 A1 | 3/2008 | Dershem | |
| 2008/0103240 A1 | 5/2008 | Dershem | |
| 2008/0142158 A1 | 6/2008 | Dershem | |
| 2008/0146738 A1 | 6/2008 | Dershem | |
| 2008/0160315 A1 | 7/2008 | Forray et al. | |
| 2008/0191173 A1 | 8/2008 | Dershem et al. | |
| 2008/0210375 A1 | 9/2008 | Dershem et al. | |
| 2008/0251935 A1 | 10/2008 | Dershem | |
| 2008/0257493 A1 | 10/2008 | Dershem | |
| 2008/0262191 A1 | 10/2008 | Mizori | |
| 2009/0061244 A1 | 3/2009 | Dershem | |
| 2009/0288768 A1 | 11/2009 | Dershem | |
| 2010/0041803 A1 | 2/2010 | Dershem | |
| 2010/0041823 A1 | 2/2010 | Dershem | |
| 2010/0041832 A1 | 2/2010 | Dershem | |
| 2010/0041845 A1 | 2/2010 | Dershem et al. | |
| 2010/0056671 A1 | 3/2010 | Dershem | |
| 2010/0063184 A1 | 3/2010 | Dershem | |

* cited by examiner

SOLUBLE METAL SALTS FOR USE AS CONDUCTIVITY PROMOTERS

RELATED APPLICATIONS

The present application claims the benefit of priority under 35 U.S.C. §119 to U.S. Provisional Application No. 61/030,948, filed Feb. 23, 2008, the contents of which is incorporated herein by reference in its entirety.

FIELD OF THE INVENTION

The present invention relates to conductivity promoters, and in particular to soluble conductivity promoters that contain a hydrocarbon moiety or a siloxane moiety and a metal. The present invention also relates to methods of making the soluble conductivity promoters of the invention and to adhesive compositions containing the conductivity promoters of the invention.

BACKGROUND

Electrical conductivity is an important property for certain categories of die attach adhesives within the field of electronic packaging and electronic component assembly. Electrical conductivity has traditionally been attained through the addition of electrically conductive fillers to liquid or film adhesive compositions. Examples of electrically conductive fillers include, for example, silver, copper, silver coated copper, gold, nickel, graphite, silver coated graphite, and the like. Frequently however, the conductivity of the compositions containing these conductive fillers is insufficient for many applications In certain instances, it is desirable to render such thermosetting resin compositions conductive, either thermally or electrically. This is typically achieved by the addition of a conductive filler, typically a metallic filler, such as silver, in particle and/or flake form. While generally the addition of the conductive filler provides adequate conductivity to the composition, in certain instances greater conductivity is desirable. Such instances include those where a microelectronic assembler desires to validate its process prior to attaching the multitude of wire bonds from the semiconductor chip to the circuit board, and thus tests for electrical conductivity at the point where the chip is attached to the board. Other instances include those where the microelectronic assembler seeks to achieve a higher degree of thermal conductivity for thermal management or heat dissipation reasons.

In some cases, it may be possible to either increase the loading level of conductive filler, select a more conductive filler, or choose a combination of fillers or particle sizes of fillers that increases conductivity. Choosing a more conductive filler or a combination of fillers or particle sizes of fillers may be satisfactory for certain applications, but it would be desirable to simply maintain the selected conductive filler, and perhaps increase its loading level. However, increasing the loading level of the conductive filler may affect adversely the rheology of the composition, thereby causing dispensing and/or flow issues. Oftentimes, increasing the loading level of the conductive filler may even adversely affect the conductivity itself. It would be desirable to be able to confer a higher level of conductivity to a thermosetting resin composition, without having to adjust the identity or the loading of the conductive filler itself.

It has previously been reported that the addition of certain metal salts can be used to improve the electrical conductivity of metal filled adhesive compositions. However, the metal salts previously used to increase electrical conductivity are insoluble or display limited solubility in conductive adhesive formulations, such as formulations containing monomers and resins. Insolubility of the metal salt additives represents a major limitation for their practical use and manufacture. The use of conductivity promoters based on insoluble salts can, for example, lead to lot-to-lot performance variability, where the solubility to the salt is greater in one lot than that in another lot.

Performance will be affected by the practical limitations of particle size and dispersion control. A consequence of this problem is significant variation in electrical performance from batch to batch, and even changes in performance during use due to changes in solubility and instability of the salt. Indeed, this drift in performance was been recognized in US 2004/0225045 A1, (paragraph [0166]) through the statement that the "compositions do not have sufficient shelf stability under ambient temperature conditions to provide reproducible results". It would thus be of interest to have conductivity promoters that operate under low temperatures compatible with the stability and reproducibility requirements of the electronics industry.

SUMMARY OF THE INVENTION

The present invention provides soluble conductivity promoters comprising a hydrocarbon moiety or a siloxane moiety and a metal. In certain embodiments, the hydrocarbon moiety can include an organic acid ligand, which may further include an acrylate, methacrylate, acrylamide, methacrylamide, maleate, fumarate, citraconate, itaconate, itaconimide, maleimide, citraconimide, vinyl ester, allyl ester, diallyl ester, triallyl ester, allyl amide, or diallyl amide functionality. The organic ligand according to the invention, typically has at least five carbons, at least about 8 carbons or at least about 10 carbon atoms. In certain aspects, the hydrocarbon moiety can be branched hydrocarbon or branched aliphatic acid.

Typical soluble conductivity promoters of the invention have a low melting temperature and can be a liquid at room temperature. In certain embodiments, the soluble conductivity promoters will be compatible with temperature ranges used in the electronics industry and thus the metal salt portion of the soluble conductivity promoters will typically decomposes to yield a free metal at a temperature less than about 220° C. and frequently less than about 200° C.

The metal of the soluble conductivity promoters according to the present invention can be Ag, Pd, Ni, Pt, and Au, for example, and most frequently is Pd.

Soluble conductivity promoters encompassed by the invention include:

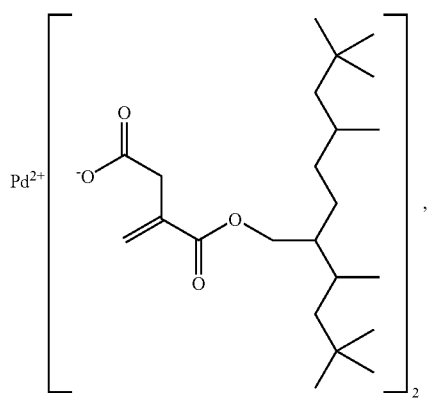

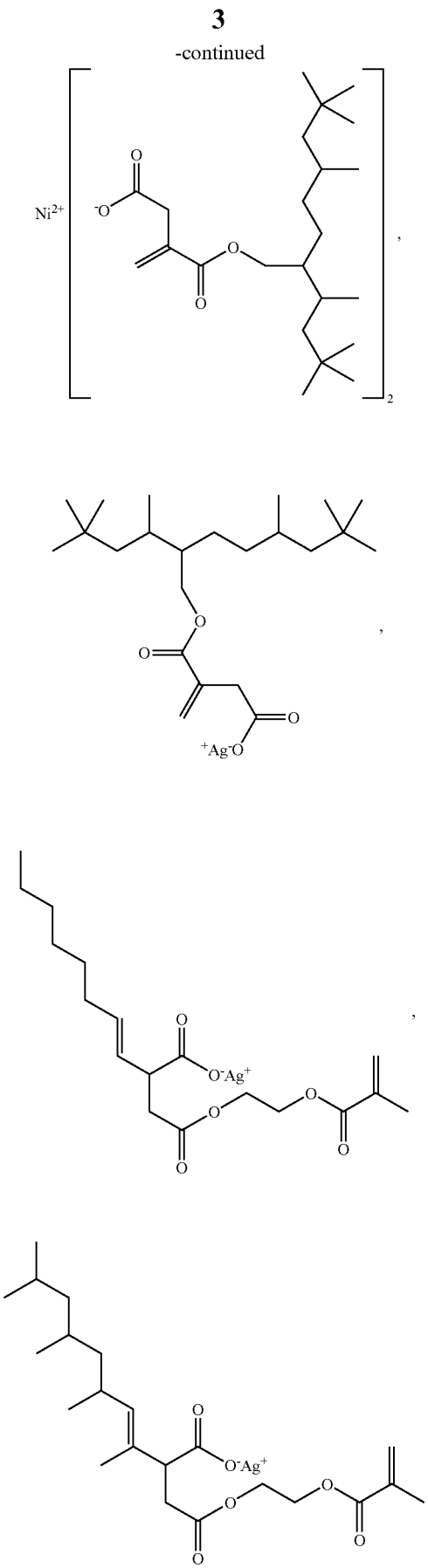

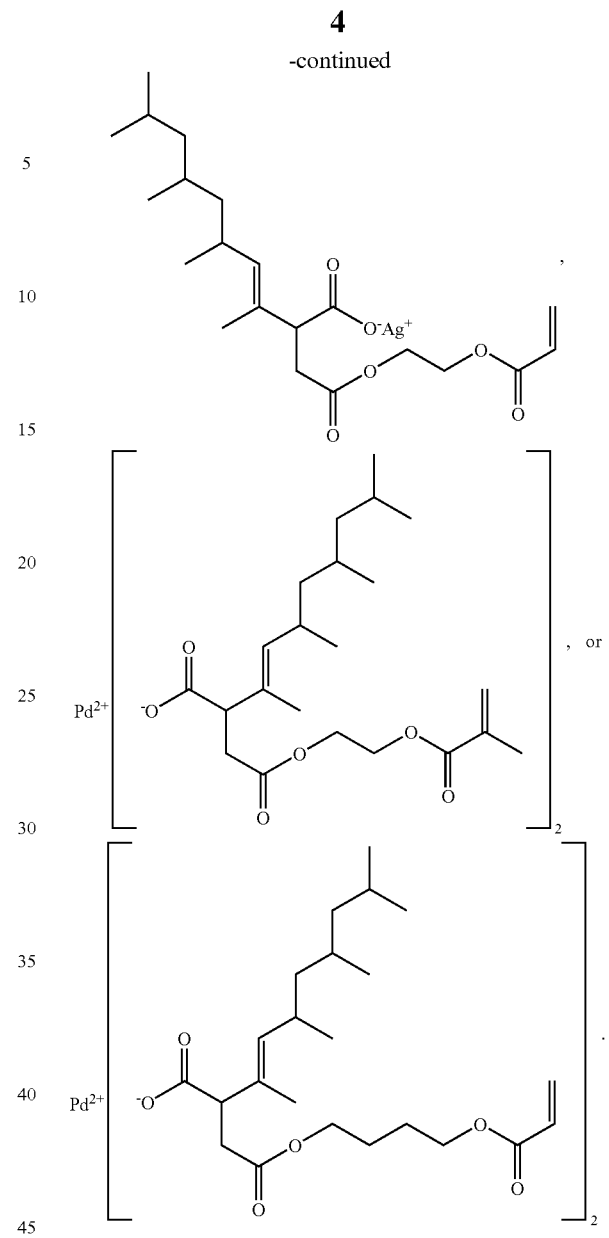

Also provided by the invention are methods for preparing a soluble conductivity promoter that include the steps of reacting a cyclic anhydride with an alcohol to generate an acid-ester and combining the acid-ester with a metal to form the soluble conductivity promoter. In another embodiment of the invention, a cyclic anhydride is reacted with an amine to generate an acid-amide and the acid-amide is combined with a metal to form a soluble conductivity promoter of the invention.

Also provided by the invention are methods for increasing the conductivity of a thermoset resin by a method of increasing the conductivity of a thermoset resin incorporating a soluble conductivity promoter described herein into the resin, and heating the resin, where the conductivity promoter decomposes to generate at least one free metal. In process of decomposition, nano-disperse metal domains may be formed within the thermoset resin.

In yet another embodiment, the present invention provides adhesive compositions that include a conductive, filled adhesive such as a silver flake filled adhesives, and a conductivity promoter of the invention, where the filled adhesive includes an organic component and a filler component. Typically, the organic component of such adhesive compositions will be about 15% of the total adhesive composition by weight and the conductivity promoter will be present at about 0.05% to about 1% of the total weight of the organic component, and frequently at about 0.6% to about 0.8% of the total weight of the organic component.

DETAILED DESCRIPTION

Figure 1B:
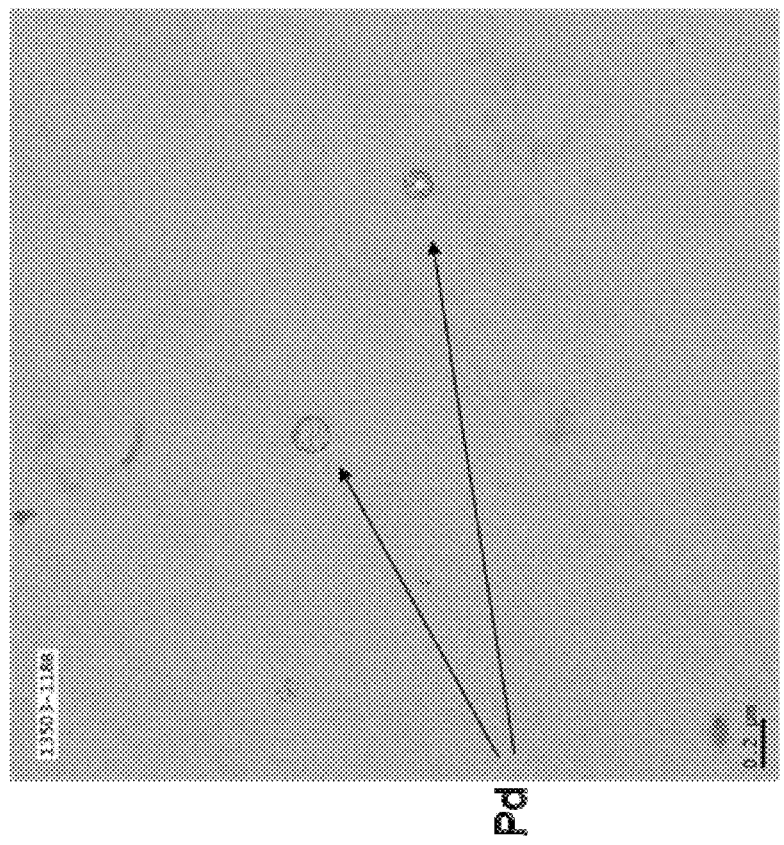
FIGS. 1A and 1B are transmission electron micrographs showing clustered palladium domains formed within a thermoset resin to which a palladium itaconate conductivity promoter of the invention was added prior to cure. (bar=0.2 µm).
Figure 1A:
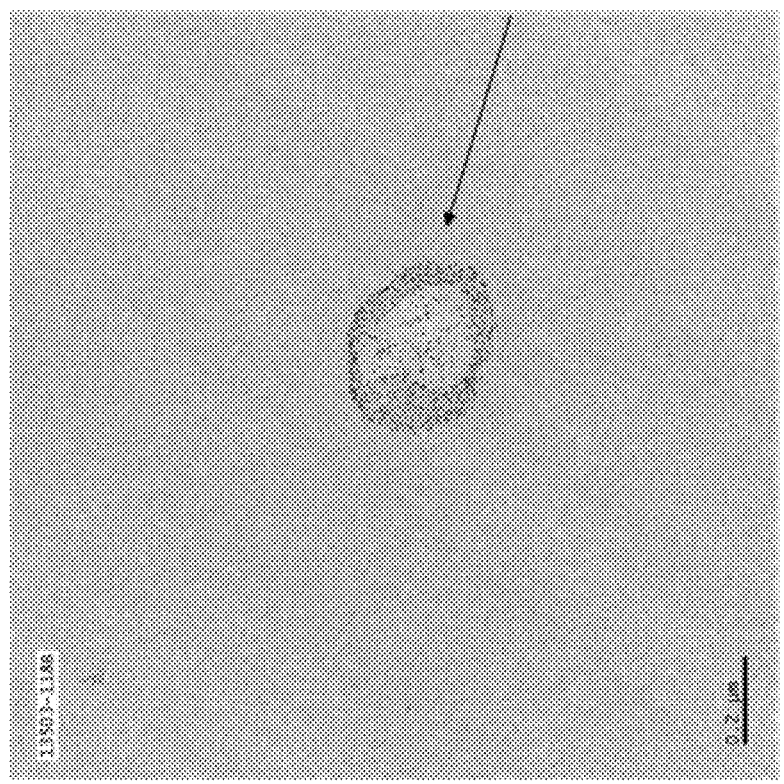

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation. The foregoing techniques and procedures can be generally performed according to conventional methods well known in the art.

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting.

The section headings used herein are for organizational purposes only and are not to be construed as limiting the subject matter described.

Whenever it appears herein, a numerical range such as "1 to 20" refers to each integer in the given range; e.g., "1 to 20 carbon atoms" means that an alkyl group can contain only 1 carbon atom, 2 carbon atoms, 3 carbon atoms, etc., up to and including 20 carbon atoms, although the term "alkyl" also includes instances where no numerical range of carbon atoms is designated.

DEFINITIONS

"About" as used herein means that a number referred to as "about" comprises the recited number plus or minus 1-10% of that recited number. For example, "about" 100 degrees can mean 95-105 degrees or as few as 99-101 degrees depending on the situation. Whenever it appears herein, a numerical range such as "1 to 20" refers to each integer in the given range; e.g., "1 to 20 carbon atoms" means that an alkyl group can contain only 1 carbon atom, 2 carbon atoms, 3 carbon atoms, etc., up to and including 20 carbon atoms, although the term "alkyl" also includes instances where no numerical range of carbon atoms is designated).

"Adhesive" or "adhesive compound" as used herein, refers to any substance that can adhere or bonds two items together. Implicit in the definition of an "adhesive composition" or "adhesive formulation" is the fact that the adhesive is a combination or mixture of more than one species, component or compound, which can include adhesive monomers, oligomers, and/or polymers along with other materials, whereas an "adhesive compound" refers to a single species, such as an adhesive polymer or oligomer.

Adhesive compositions, in particular, refers to un-cured adhesives compositions in which the individual components in the mixture retain the chemical and physical characteristics of the individual components of which the mixture is made. Adhesive compositions are typically malleable and may be liquids, paste, gel or another form that can be applied to an item so that is can be bonded to another item.

"Cured adhesive," cured adhesive composition" or "cured adhesive compound" refers to adhesives which have undergone a chemical and/or physical changes such that the mixtures is transformed into a solid, substantially non-flowing material which curing process may involve e.g. crosslinking.

As used herein, "aliphatic" refers to any alkyl, alkenyl, cycloalkyl, or cycloalkenyl moiety.

"Aromatic hydrocarbon," as used herein, refers to compounds having one or more benzene rings.

"Alkane," as used herein, refers to saturated straight-chain, branched or cyclic hydrocarbons having only single bonds. Alkanes have general formula $C_nH_{2n+2}$.

"Cycloalkane," refers to an alkane having one or more rings in its structure. As used herein, "alkyl" refers to straight or branched chain hydrocarbyl groups having from 1 up to about 100 carbon atoms. Whenever it appears herein, a numerical range, such as "1 to 100" or "$C_1$-$C_{100}$", refers to each integer in the given range; e.g., "$C_1$-$C_{100}$ alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated). "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, amido, —C(O)H, —C(O)—, —C(O)O—, —S—, —S(O)$_2$, —OC(O)—O—, —NR—C(O), —NR—C(O)—NR, —OC(O)—NR, wherein R is H or lower alkyl, acyl, oxyacyl, carboxyl, carbamate, sulfonyl, sulfonamide, sulfuryl, and the like.

As used herein, "cycloalkyl" refers to cyclic ring-containing groups typically containing in the range of about 3 up to about 8 carbon atoms, and "substituted cycloalkyl" refers to cycloalkyl groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

As used herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above. The term heterocyclic is also intended to refer to heteroaromatic moieties. As used herein, "alkenyl" refers to straight or branched chain hydrocarbyl groups having at least one carbon-carbon double bond, and having in the range of about 2 up to about 100 carbon atoms, and "substituted alkenyl" refers to alkenyl groups further bearing one or more substituents as set forth above.

"Allyl" as used herein, refers to refers to a compound bearing at least one moiety having the structure:

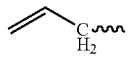

"Imide" as used herein, refers to a functional group having two carbonyl groups bound to a primary amine or ammonia. The general formula of an imide of the invention is:

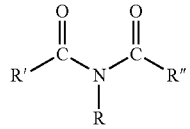

"Polyimides" are polymers of imide-containing monomers. Polyimides typically have one of two forms: linear or cyclic. Non-limiting examples of linear and cyclic (e.g. an aromatic heterocyclic polyimide) polyimides are shown below for illustrative purposes.

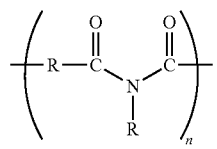

Linear Polyimide

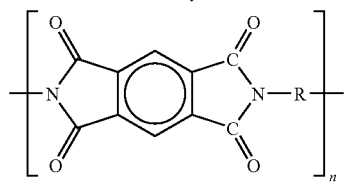

Aromatic Heterocyclic Polyimide

"Maleimide," as used herein, refers to an N-substituted maleimide having the formula as shown below:

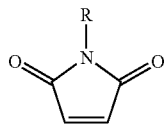

where the "R" group may be an aromatic, herteroaromatic, aliphatic, or polymeric moiety.

"Bismaleimide" or "BMI", as used herein, refers to a compound having the general structure shown below:

BMIs can cure through an addition rather than a condensation reaction, thus avoiding problems with volatiles forming. It can be produced by a vinyl-type polymerization of a pre-polymer terminated with two maleimide groups.

As used herein, the term "acrylate" refers to a compound bearing at least one moiety having the structure:

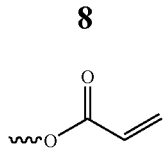

As used herein, the term "acrylamide" refers to a compound bearing at least one moiety having the structure:

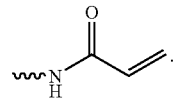

As used herein, the term "methacrylate" refers to a compound bearing at least one moiety having the structure:

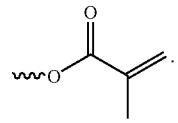

As used herein, the term "methacrylamide" refers to a compound bearing at least one moiety having the structure:

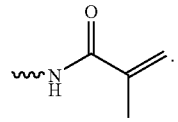

As used herein, the term "citraconimide" refers to a compound bearing at least one moiety having the structure:

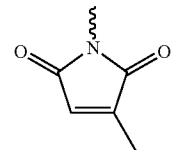

As used herein "epoxy" refers to a thermosetting epoxide polymer that cures by polymerization and crosslinking when mixed with a catalyzing agent or "hardener," also referred to as a "curing agent" or "curative." Epoxies of the present invention include, but are not limited to aliphatic, cycloaliphatic, glycidyl ether, glycidyl ester, glycidyl amine epoxies, and the like, and combinations thereof. Epoxies of the invention include compounds bearing at least one moiety having the structure:

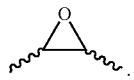

As used herein, the term "vinyl ether" refers to a compound bearing at least one moiety having the structure:

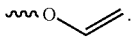

"Thermoplastic," as used herein, refers to the ability of a compound, composition or other material (e.g. a plastic) to melt to a liquid when heated and freeze to solid, often brittle and glassy, state when cooled sufficiently.

"Thermoset," as used herein, refers to the ability of a compound, composition or other material to irreversibly "cure" to a stronger, harder form. Thermoset materials are typically polymers that may be cured, for example, through heat (e.g. above 200 degrees Celsius), via a chemical reaction (e.g. epoxy), or through irradiation (e.g. U.V. irradiation).

Thermoset materials, such as thermoset polymers or resins, are typically liquid or malleable forms prior to curing, and therefore may be molded or shaped into their final form, and/or used as adhesives. Curing transforms the thermoset resin into a rigid infusible solid or rubber by a cross-linking process. Thus, energy and/or catalysts are added that cause the molecular chains to react at chemically active sites (unsaturated or epoxy sites, for example), linking the polymer chains into a rigid, 3-D structure. The cross-linking process forms molecules with a higher molecular weight and resultant higher melting point. During the reaction, when the molecular weight of the polymer has increased to a point such that the melting point is higher than the surrounding ambient temperature, the polymer becomes a solid material.

"Cross-linking," as used herein, refers to the attachment of two or more polymer chains by bridges of an element, a molecular group, or a compound. In general, crosslinking of the compounds of the invention takes place upon heating. As cross-linking density is increased, the properties of a material can be changed from thermoplastic to thermosetting.

The present invention is based on the notion that a significant improvement in conductive additive performance can be achieved through the preparation of metal salts that are soluble in, and remain soluble in, the adhesive compositions, such as thermoset resin systems, into which they are formulated. This can be accomplished by preparing salts of certain metals that include hydrocarbon or siloxane moieties that are sufficiently large so as to render the resulting salt soluble in the chosen adhesive compositions, such as in thermoset adhesive compositions used in the electronics industry. The skilled artisan will recognized that thermoset adhesives, and particularly those used in demanding electronics applications, should not be exposed to temperatures above about 220° C., and preferably, should be kept below 200° C.

Sufficiently large moieties that can be included in the salts of the invention include branched aliphatic acid ligands. Advantageously, the branching in the aliphatic side chain depresses the melting points of the resulting salts. Salts that either have low melting points or are liquids at room temperature are easier to dissolve in initially and are more likely to remain in solution during storage, use in the adhesive composition, and eventual conductive application in the cured adhesive.

In certain embodiments, an additional polymerizable moiety is incorporated into the ligands used to make the soluble metal salts according to the invention. The organic acid ligand may, for example, include an acrylate, methacrylate, acrylamide, methacrylamide, maleate, fumarate, citraconate, itaconate, itaconimide, maleimide, citraconimide, vinyl ester, allyl ester, diallyl ester, triallyl ester, allyl amide, diallyl amide, thiol, phenol, or oxetane functionality.

The organic acid ligand typically has at least five carbons, frequently at least eight carbons, and often at least ten carbon atoms. As discussed above, one or more branches in the hydrocarbon backbone of the organic acid ligand will depress the melting points of the resulting salts and therefore can be included as a desirable feature.

The organic acid ligand of the invention can be a commercially available carboxylic acid or any other organic acid that meets the requirements set forth above. In certain embodiments, acid ligands suitable for making the salts of the invention can be prepared by reaction of cyclic anhydrides with alcohols or amines to generate ester-acids and amide-acids, respectively. This method of organic acid ligand synthesis provides a wide range of soluble metal ligands for salt synthesis. Cyclic anhydrides that are especially attractive for use in this invention include those which contain a polymerizable functionality. Examples of such functional cyclic anhydrides include itaconic anhydride, citraconic anhydride, maleic ahydride, phenylmaleic anhydride, nadic anhydride, methylnadic anhydride and allylsuccinic anhydride. The reaction of these anhydrides with an alcohol or amine produces the corresponding acid-ester or acid-amide.

The reaction of branched and/or higher molecular weight alcohols with maleic anhydride results in organo-soluble mono-maleates. The residual double bond in these acid-esters would permit the preparation organo-soluble metal salts that are suitable for incorporation into the matrix of thermoset compositions via free-radical cure. The double bond of the mono-maleate can also be thermally isomerized to yield a mono-fumarate. The soluble metal salts of the mono-fumarate thus, can also be readily co-polymerized into a thermoset matrix via free-radical cure.

In certain other aspects of the invention, branched and/or higher molecular alcohols can be reacted with the other unsaturated cyclic anhydries to generate organo-soluble mono-itaconates, citraconates, phenylmaleates, nadates, methylnadates, and allylsuccinates. All of these acid-esters are suitable for use in the preparation of polymerizable, ogano-soluble metal salts.

An alternative to having a polymerizable functional group within the cyclic anhydride starting material is to prepare an acid-ester wherein the starting alcohol possesses a polymerizable moiety. Anhydrides that can be used for this include succinic anhydride; octenylsuccinic anhydride; dodecenylsuccinic anhydride; octadecenylsuccinic anhydride; phenylsuccinic anhydride; 1,2-cyclohexanedicarboxylic anhydride; 1,2,3,6-tetrahydrophthalic anhydride; 3,4,5,6-tetrahydrophthalic anhydride; phthalic anhydride; 4-methylphthalic anhydride; tetrachlorophthalic anhydride; tetrabromophthalic anhydride; 2,3-diphenylmaleic anhydride; 2-phenylglutaric anhydride; 1,8-naphthalic anhydride; diphenic anhydride; homophthalic anhydride; isatoic anhydride; N-methylisatoic anhydride; glutaric anhydride; 2,2-dimethylglutaric anhydride; 3,3-dimethylglutaric anhydride; hexahydro-4-methylphthalic anhydride; isobutenylsuccinic anhydride; 2,3-dimethylmaleic anhydride; 2,2-dimethylsuccinic anhydride; 3,3-tetramethyleneglutaric anhydride; 3-ethyl-3-methylglutaric anhydride; 3-methylglutaric anhydride; methylsuccinic anhydride; tetrapropenylsuccinic anhydride; and the like. Alcohols that possess polymerizable moieties include 2-hydroxyethyl methacrylate; hydroxypropyl methacrylate; 2-hydroxyethyl acrylate; hydroxypropyl acryate; 4-hydroxybutyl acrylate; 4-hydroxybutyl methacrylate; 2-hydroxyethyl acrylamide; 2-hydroxyethyl methacrylamide; allyl alcohol, poly(propylene glycol) methacrylate; poly(propylene glycol) acrylate; poly(ethylene glycol) methacrylate; polycaprolactone diol mono-2-hydroxyethylacrylate; polycaprolactone diol mono-2-hydroxyethylmethacrylate; N-(2-hydroxyethyl)maleimide; N-(2-hydroxyethyl) citraconimide; N-hydroxypropylmaleimide; N-hydroxypropylcitraconimide; 5-norbornene-2-methanol; 5-norbornene-2-ol; 2-mercaptoethanol; 3-ethyl-3-hydroxymethyl oxetane; 4-hydroxybenzyl alcohol; 2-(4-hydroxyphenyl)ethyl alcohol; and the like.

Ester-acids suitable for use in the present invention also include those in which both the cyclic anhydride and alcohol starting materials contain a polymerizable functional group, such as the reaction product of 4-hydroxybutyl acrylate and itaconic anhydride. Many suitable, dual polymerizable, acid-ester combinations are envisioned for use in the present invention.

Representative acid-ester precursors for the organo-soluble salts are shown as exemplary compounds A-1 through A-15. It will be understood by one skilled in the art that where an acid-ester is prepared from an asymmetrical anhydride, such as itaconic anhydride, two possible acid-ester products would be produced. One product would have the free acid adjacent to the carbon-carbon double bond in the backbone, while in the other it would be adjacent to a methylene moiety. For simplicity, only one product is shown for acid-ester compounds A-1, A-3, and A-13 below:

Compound A-1

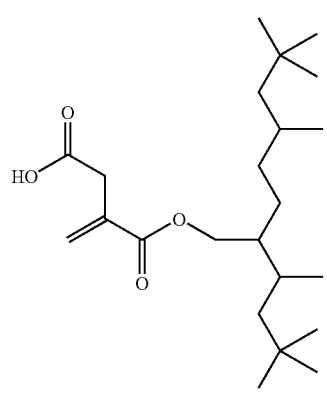

Compound A-2

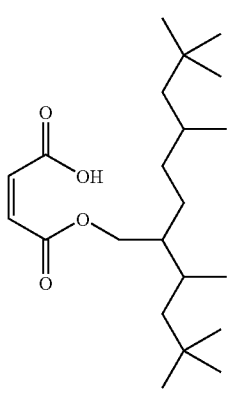

Compound A-3

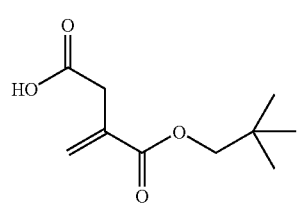

Compound A-4

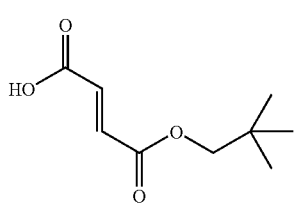

Compound A-5

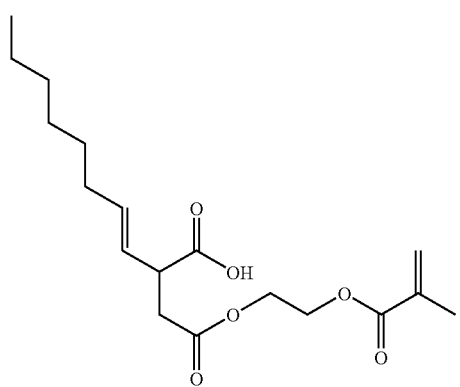

Compound A-6

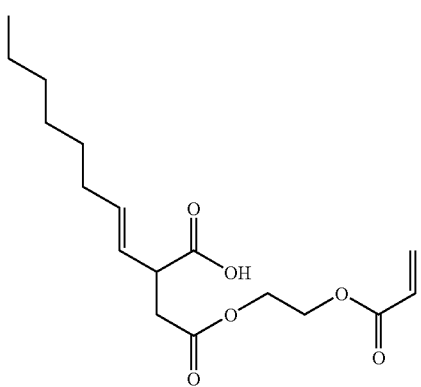

Compound A-7

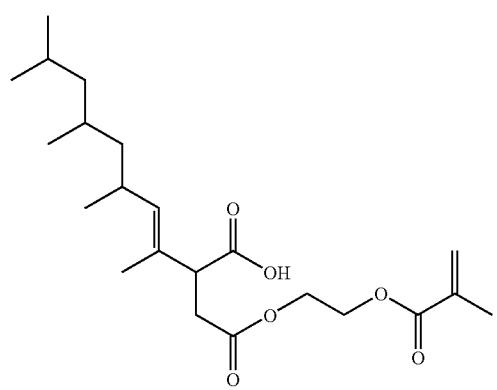

Compound A-8

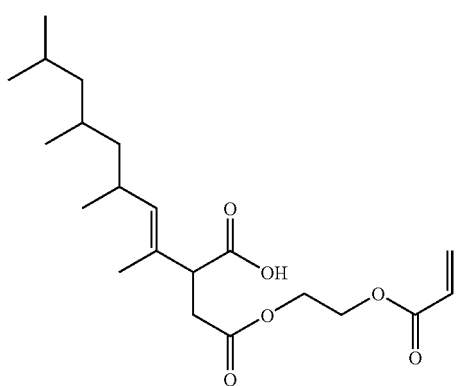

-continued
Compound A-9
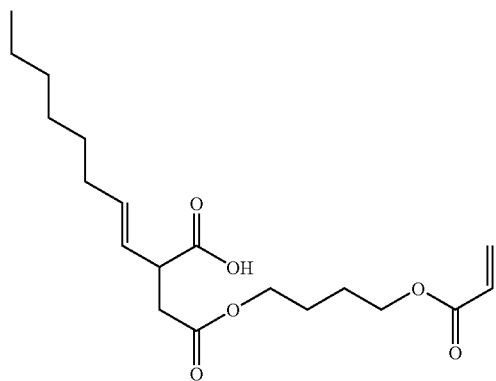
Compound A-10
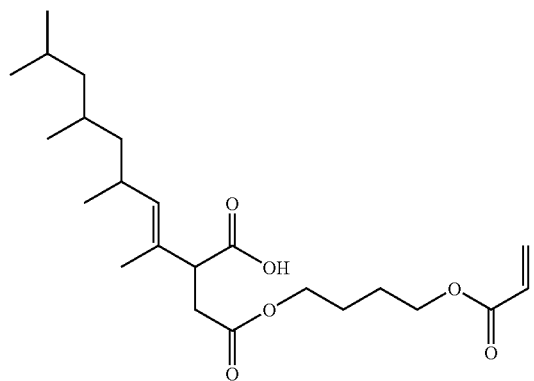
Compound A-11
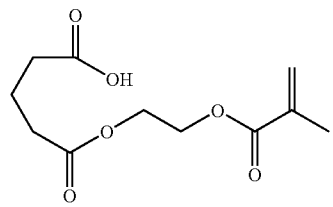
Compound A-12
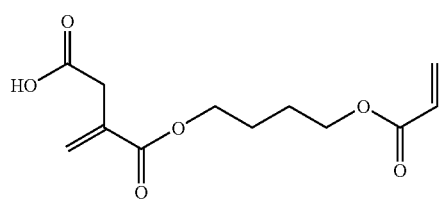
Compound A-13
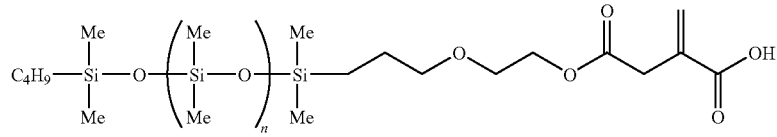
Compound A-14
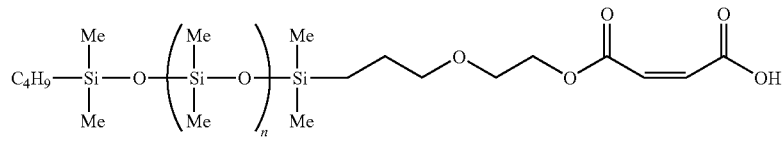
Compound A-15
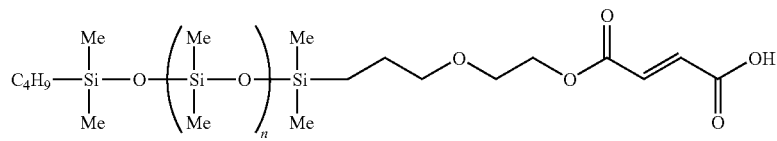
Exemplary metal salt conductivity promoters of the invention include:
Compound S-1
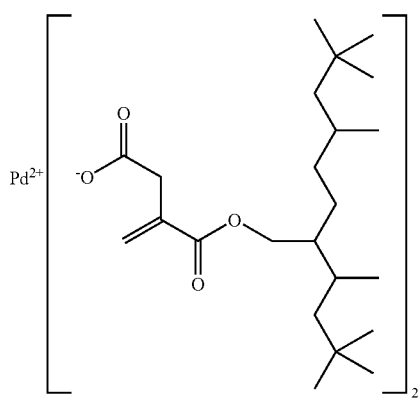
-continued
Compound S-2
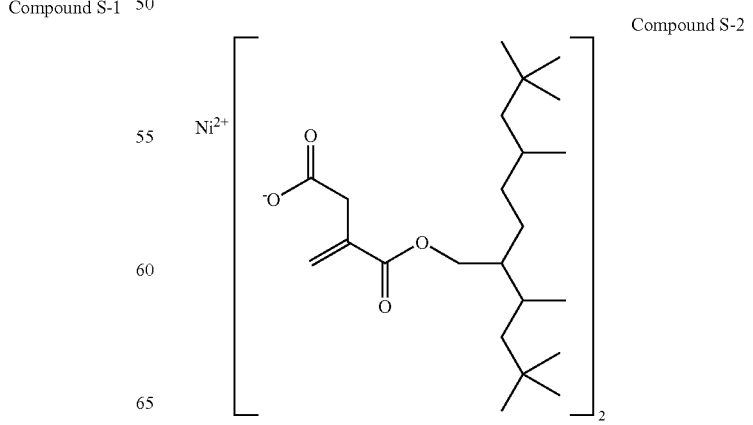

Compound S-3

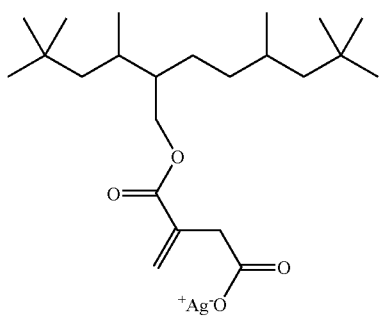

Compound S-4

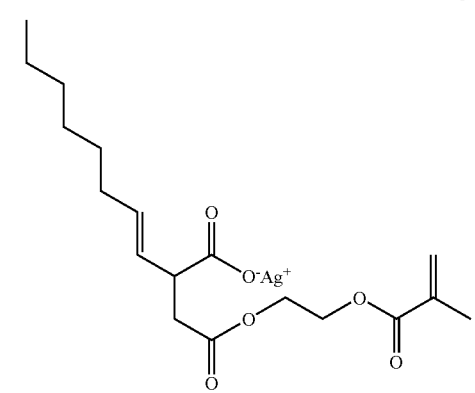

Compound S-5

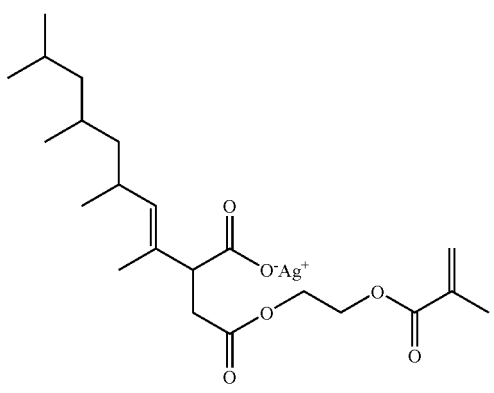

Compound S-6

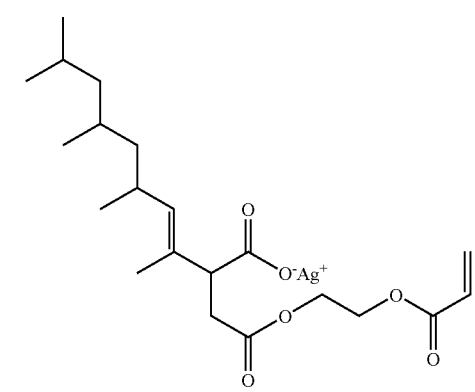

Compound S-7

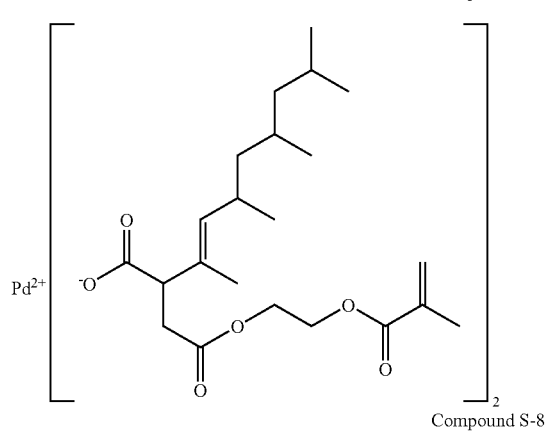

Compound S-8

Compound S-9

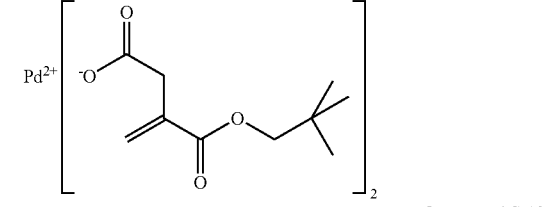

Compound S-10

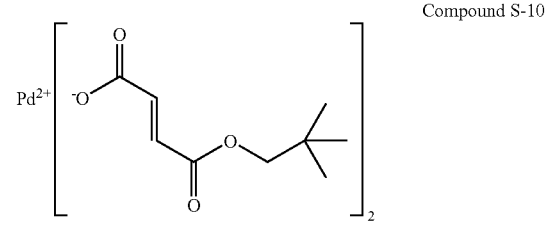

Typically, the metal used for the preparation of metal salts of the invention is Pd. In addition Ag, Ni, Pt, and Au may also be used in certain embodiments. Many of the salts made from Ag, Pd, Ni, Pt, and Au decompose thermally to generate free metal atoms. Each of these can directly decompose to the free metal instead of a non-conductive metal oxide.

In one embodiment, the compounds of the invention promote conductivity by increasing electrical conductivity only after thermal decomposition of the salt has been accomplished. This is in contrast to other reported metal salts that are believed to increase electrical conductivity via an ionic mechanism.

Figure 3:
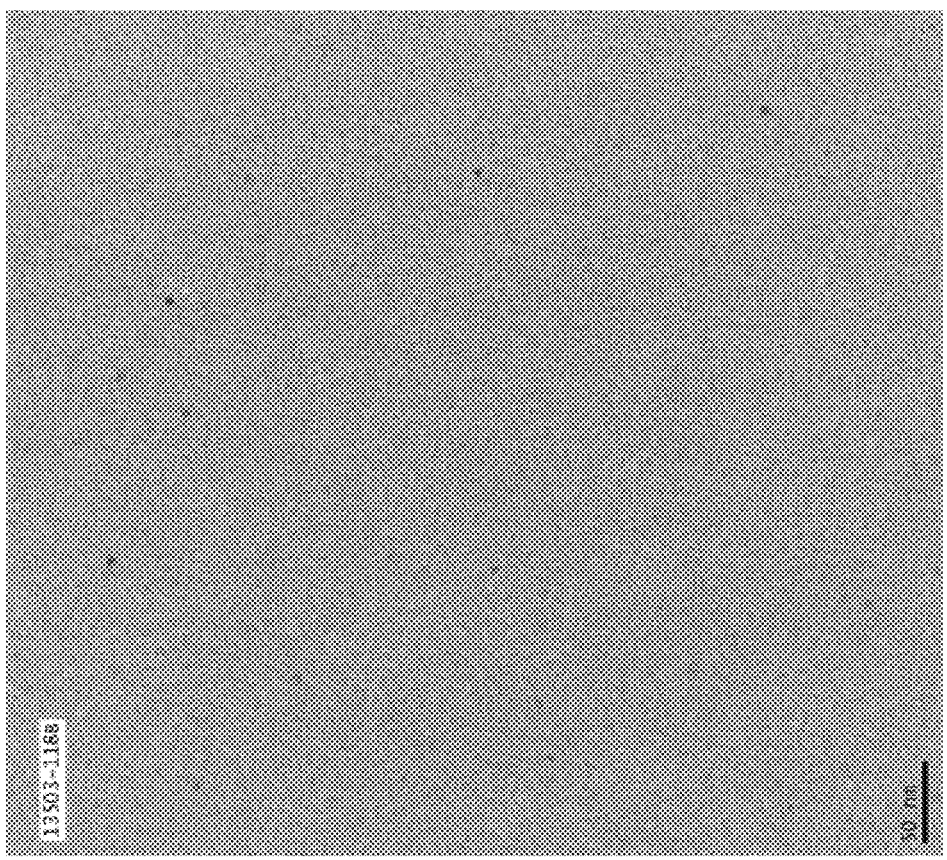
FIG. 3 shows nano-dispersed palladium domains formed as in FIGS. 1A, 1B, 2A, and 2B (bar=50 nm).

The conductivity promoters of the present invention provide intrinsically superior electrical conductivity performance. The generation of nano-disperse metal domains within the insulating thermoset resin matrix as shown in FIG. 3 are believed to work synergistically with the conductive fillers and provide a stable path for the flow of electrons through the cured adhesive. Insoluble, conductivity-promoting salts are thought to enhance conductivity through the presence of free metal ions and are therefore susceptible to environmental factors such as humidity. Furthermore, even if the previously described additives decompose to free metals in situ during cure, the resulting metallic domain size would be approximately of the same dimensions of the original salt particle and would not result in a nano-disperse electrically conductive path. Nano-disperse particles are superior for many applications because such particles can lead to the formation of an electrically conductive path and are critical to the performance of the compounds of this invention. Silver flake is the filler of choice for most electrically conductive adhesives. Not only is silver an excellent conductor of electricity, it is a relatively noble metal and therefore resistant to oxidation. Even when oxidation of silver occurs, its oxide is also conductive. Despite these benefits, however, there are inherent limits on the electrical conductivity of silver-filled organic adhesives. Silver is a very dense metal with a room temperature density of approximately 10.5 g/cc. Thus, a silver-filled organic adhesive containing 85% by weight silver contains only about 35% by volume of the metal (assuming a density of 1.0 for the organic portion). The organic portion of the adhesive is an electrical insulator. The compounds of this invention provide a mechanism to improve the electrical conductivity of the cured silver-organic matrix above and beyond what the silver filler by itself can do. The presence of a soluble, polymerizable, thermally labile, noble metal salt in the organic matrix of the composition provides a mechanism to improve the electrical performance of the cured composite. It is believed that the formation of nano-disperse metallic domains within the organic matrix reduces the electrical resistance of the organic phase of the cured adhesive. The presence of these nano-disperse metallic domains is believed to provide alternative electrical pathways that supplement the point-to-point contacts of the silver filler within the cured matrix.

In another aspect of the invention, the acid ligand contains polymerizable functional groups. This aspect of the invention work synergistically with the inherent solubility of the metal salts to produce a nano-disperse matrix within the organic phase of the cured adhesive composition. The presence of a polymerizable moiety within the acid ligand reduces the tendency of the conductive additive to phase separate into large pools within the polymer matrix during cure. Instead, the polymerizable moiety allows the organic acid ligand portion of the conductivity promoters of the invention to cure into the and therefore become a part of the adhesive composition during cure. The acid ligand, dispersed throughout the adhesive formulation during adhesive preparation and mixing, can be fixed in place throughout the adhesive rather than be allowed to pool or localized to an area(s). The presence of reactive functionality within the acid ligand of the invention compounds insures the formation of a more homogeneous dispersion of conductive metal particles within the cured organic phase.

The polymerizable functional groups may be in the form of reactive, ethylenic unsaturation. Examples of reactive carbon-carbon double bond containing moieties would include acrylate, methacrylate, acrylamide, methacrylamide, allyl, allylamide, diallylamide, maleimide, citraconimide, itaconate, citraconate, maleate, fumarate, phenylmaleate, nadate, methylnadate, and allysuccinate. Acid ligands containing reactive unsaturation are most useful where the base monomer composition comprises free radically polymerizable monomers. Other polymerizable groups that are contemplated in this invention include thiols, phenols, and oxetanes. These later functionalities are preferred for use, for example, in epoxy-based adhesive compositions.

The present invention also provides adhesive compositions containing the conductivity promoters of the invention. Conductive adhesive compositions of the invention will typically contain an organic component and a conductive filler, such as a silver flake filler. In certain embodiments of the invention, the organic component comprises about 10 to about 20% of the total adhesive composition by weight. In other embodiments, the organic component comprises about 15% of the total adhesive composition by weight. The present invention provides conductive adhesive compositions that further contain a conductivity promoter described herein at approximately 0.8% of the total weight of the organic component of the adhesive composition.

EXAMPLES

Example 1

Preparation of Isooctadecyl Mono-Itaconate
(Compound A-1)

A single neck, 250 ml flask was charged with 12.33 g (0.11 mole) itaconic anhydride, and 27.0 g (0.10 mole) isooctadecyl alcohol. The flask was rotated in a water bath set at 65° C. The mix appeared initially as a slurry of the solid itaconic anhydride in the alcohol. It was transformed to a hazy homogeneous liquid within the first three hours of mixing. The heating was continued for 16.5 hours. The product was then dissolved in 100 ml octane and this solution was passed over 10.5 g silica gel. The octane was removed on a rotary evaporator (vacuum followed by sparge with clean dry air) to yield 36.0 g (94.2% of theory) of the acid-ester as a clear, light-yellow, viscous liquid. An FTIR spectrum of compound demonstrated prominent absorptions at 2951, 1738, 1698, 1634, 1467, 1364, 1156, 1006, 954, and 826 wavenumbers.

Example 2

Preparation of Neopentyl Mono-Itaconate
(Compound A-3)

A 125 ml, single-neck flask was charged with 22.4 g (0.20 mole) itaconic anhydride and 20.2 g (0.23 mole) neopentanol. This mixture was heated and stirred at 85° C. for four hours the excess neopentanol was then sparged out of the mixture to yield 37.3 g (93.4% of theory) of what was at first a clear liquid. The compound transformed to a white waxy solid upon sitting at room temperature. An FTIR was performed on this compound and it was found to have prominent absorptions at 2959, 1728, 1703, 1637, 1318, 1190, and 1162 wavenumbers.

Example 3

Preparation of Isooctadecyl Mono-Maleate
(Compound A-2)

A 250 ml, one-neck flask was charged with 27.0 g (0.10) mole isooctadecyl alcohol and 12.0 g (0.122 mole) maleic anhydride. This mix was stirred overnight at 60° C. overnight. The product was then dissolved in 100 ml toluene and the solution was filtered over 10 g silica gel. The residual volatiles were removed via sparging to yield 35.16 g (96.4% of theory) of a colorless viscous liquid. An FTIR was performed on this compound and it was found to have prominent absorptions at 2953, 1732, 1709, 1634, 1166, and 820 wavenumbers.

Example 4

Preparation of Compound A-13

A 250 ml, one-neck flask was charged with 11.2 g (0.10 mole) itaconic anhydride and 40.0 g (approximately 0.04 mole) MCR-C12 (Gelest Inc., Morrisville, Pa.). This mixture was stirred at 65° C. for twenty-one hours. The flask was then charged with 100 ml of octane. The octane solution was then filtered over 15 g of silica gel. The octane was removed to yield 40.5 g of a clear colorless liquid. An FTIR was performed on this compound and it was found to have prominent absorptions at 2961, 1746, 1704, 1257, 1017, 790, and 700 wavenumbers.

Example 5

Preparation of Compound S-9

A mixture containing 20.0 g (0.10 mole) of the neopentyl mono-itaconate from Example 2 and 11.22 g (0.050 mole) palladium acetate was ground together in a mortar and pestle. This solid mixture was then transferred to a one-neck, 250 ml flask. The flask was slowly rotated in a water bath set at 60° C. for two hours to initiate an exchange reaction between the palladium acetate and the itaconate acid-ester. The flask was then sparged with clean, dry air for five hours while the flask and its contents were rotated in the 60° C. water bath. The product was initially a very viscous liquid that set to a brown-black waxy solid upon cooling to room temperature. It weighed 25.17 g (99.8% of theory). A TGA was performed on this compound (ramp rate=10° C./minute, air purge). The compound was found to have a decomposition onset temperature of 141° C. The residual weight at 400° C. was 21.82 percent (note: the theoretical palladium content of this salt was 21.1%).

Example 6

Preparation of Compound S-3

A 125 ml, one-neck flask was charged with 7.65 g (0.020 mole) of the isooctadecyl mono-itaconate from Example 1 and 6.96 g (0.030 mole) silver(I) oxide and 50 ml toluene. This mixture was rotated overnight in a water bath at 65° C. The black suspension was then filtered over 7.0 g silica gel and the toluene was removed under vacuum on a rotary evaporator and sparge (both at 65° C.) to yield 8.28 g (84.6% of theory) of a clear, red, sticky, semi-solid. A TGA was performed on this compound (ramp rate=10° C./minute, air purge). The compound was found to have a decomposition onset temperature of 172° C. The residual weight at 500° C. was 20.6 percent (note: the theoretical silver content of this salt was 22.0%).

Example 7

Preparation of Compound S-11

A 250 ml, one-neck flask was charged with 18.43 g (0.050 mole) of the isooctadecyl mono-maleate from Example 3, 7.0 g (0.030 mole) silver(I) oxide, and 50 ml toluene. This mixture was stirred for one hour at 60° C. The mix was then passed over 10 g silica gel. The solvent was removed to yield 23.24 g (97.8%) of what became an amber waxy solid at room temperature.). A TGA was performed on this compound (ramp rate=10° C./minute, air purge). The compound was found to have a decomposition onset temperature of 238° C. The residual weight at 450° C. was 22.71 percent (note: the theoretical palladium content of this salt was 22.69%). It was observed that this material formed what appeared to be a shinny, continuous, silver film on glass after being heated for four hours at 200°.

Example 8

Preparation of Compound S-1

A mixture containing 30.6 g (0.080 mole) of the isooctadecyl mono-itaconate from Example 1 (Compound A-1), 8.98 g (0.040 mole) palladium acetate and 20 ml toluene were placed into a one-neck, 250 ml flask. The flask was rotated in a water bath set at 60° C. for 0.5 hour to initiate an exchange reaction between the palladium acetate and the itaconate acid-ester. The flask was then sparged with clean, dry air for one hour while the flask and its contents were rotated in the 60° C. water bath. A fresh 20 ml portion of toluene was added to the flask and the flask was swirled to dissolve the product. The flask was returned to the rotary evaporator and sparged at 60° C. for another hour. This process was repeated one more time. The product was a very viscous brown-black liquid upon cooling to room temperature. It weighed 34.24 g (98.5% of theory). A TGA was performed on this compound (ramp rate=10° C./minute, air purge). The compound was found to have a decomposition onset temperature of 154° C. The residual weight at 400° C. was 13.39 percent (note: the theoretical palladium content of this salt was 12.24%).

Example 9

Compound S-1 Reduces Electrical Resistivity

Two silver-filled die attach adhesive test compositions were formulated. One of these compositions contained the palladium salt from Example 8. The other was a control. The composition for these two formulations is summarized in Table 1.

TABLE 1

Die Attach Adhesive Test Compositions

| Component | Conductive Test Composition 1-A | Comparative Test Composition 1-B |
|---|---|---|
| Ricon 130MA20, Polybutadiene Adducted With Maleic Anhydride[a] | 1.093 | 1.202 |
| PEAM 1044[b] | 7.103 | 7.103 |
| SR833S, Tricyclodecane Dimethanol Diacrylate[a] | 1.448 | 1.448 |
| SR423A, Isobornyl Methacrylate | 1.423 | 1.423 |
| SR368D, Tris (2-Hydroxy Ethyl) Isocyanurate Triacrylate[a] | 2.186 | 2.186 |
| Dicumyl Peroxide | 0.546 | 0.546 |
| Example 8 Compound | 0.109 | — |

TABLE 1-continued

Die Attach Adhesive Test Compositions

| Component | Conductive Test Composition 1-A | Comparative Test Composition 1-B |
|---|---|---|
| A186, Epoxy Cyclohexyl Trimethoxy Silane[c] | 0.546 | 0.546 |
| A187, Glycidoxy propyl trimethoxy silane[c] | 0.273 | 0.273 |
| A174NT, Gamma-Methacryloxypropyltrimethoxysilane[c] | 0.273 | 0.273 |
| Silver Flake SF-80[d] | 40.0 | 40.0 |
| Silver Flake EA-30[e] | 45.0 | 45.0 |

Notes:
[a]Sartomer Company, Inc.;
[b]U.S. Pat. No. #7,285,613 B2, Example 3;
[c]GE Silicones;
[d]Ferro Corporation;
[e]Metalor USA The two die attach adhesives from Table 1. were used to bond 150×150 mil silicon die to various leadframes. The parts were cured in an oven that was ramped from room temperature to 175° C. at 10° C. per minute followed by a fifteen-minute soak at 175° C. Six parts of each of the test die attach adhesive were made on all three of the leadframe types tested. The parts were then placed into boiling, deionized water for five hours (as part of an accelerated moisture resistance test). The adhesion of the silicon die to the leadframes was tested at 260° C. using a Dage 4000 die shear tester. Serpentine patterns of these pastes were also deposited onto glass microscope slides via a stencil and then cured according to the same schedule. The volume resistivity of the cured serpentine patterns was measured using a four-point probe technique. The resistivity for each of the cured die attach adhesives were measured for two different samples, and the final resistivity reported was the average of those two test parts. The results of these tests are summarized in Table 2.

TABLE 2

Die Shear Strength and Volume Resistivity

| Substrate | Die Attach Composition 1-A | Die Attach Composition 1-B |
|---|---|---|
| Copper | 5.8 ± 1.9[a] | 6.1 ± 1.6[a] |
| Silver-Spot | 1.6 ± 0.1[a] | 2.2 ± 0.5[a] |
| Palladium Plated | 7.6 ± 0.9[a] | 8.0 ± 2.3[a] |
| Glass | 0.00008[b] | 0.001[b] |

Notes:
[a]Kilograms force;
[b]ohm-cm

The results summarized in Table 2. demonstrate a remarkable reduction in electrical resistivity achieved by the addition of approximately 0.11% of the conductivity promoter of Example 8. The adhesion on all of the leadframe types was somewhat lower than the control, but still within the normal distribution of those of the control composition.

Example 10

Comparison of Conductivity Promoters on Conductivity of Adhesive Compositions

An exemplary conductive adhesive composition was prepared having the composition shown in Table 3. below:

TABLE 3

Composition of Silver Filled Test Adhesive Base Composition

| Component | Percent | Target Weight, mg |
|---|---|---|
| Silver Flake SF80[a] | 40.00 | 6000.0 |
| Silver Flake EA-0030[b] | 40.00 | 6000.0 |
| PEAM 1044[c] | 15.33 | 2299.5 |
| Tricyclodecane Dimethanol Diacrylate[d] | 4.47 | 670.5 |
| tert-Butyl peroxy-2-ethylhexanoate[e] | 0.20 | 30.0 |
| Total | 100.00 | 15000.0 |

Notes:
[a]Silver flake, Ferro Corporation, Cleveland, Ohio;
[b]Silver Flake; Metalor USA, North Attleboro, MA;
[c]U.S. Pat. No. #7,285,613 B2, Example 3;
[d]SR833S, Sartomer Company, Inc;
[e]TRIGANOX 21, Akzo Nobel Chemicals, Inc.

The conductivity promoter adipic acid, SP#1 (a blend of low molecular weight dibasic acids), or Compound S-1 (Example 8) were added to the adhesive composition at various concentrations from 0% to 1.0%. The adhesive composition containing the conductivity promoter was cured and the volume resistivity (VR; ohm-cm) was measured post cure and post mould. As has previously been reported, adipic acid reduced post cure VR and the effect was most pronounced at a concentration of 0.2% of the base mix. Post mould VR was not affected. SP#1 had a similar effect and the post cure VR was even lower throughout the range tested.

In contrast, Compound S-1 improved VR both post cure and post mould. Of the conductivity promoters tested, only Compound S-1 improved VR post cure and post mould, with an optimal concentration of 0.8% of organic compounds observed. Further addition of neither adipic acid nor SP#1 to the Compound S-1-containing adhesive composition affected the VR further, when the optimal amount of Compound S-1 was added.

Example 11

Nano Dispersion of Palladium Particles from Soluble Conductivity Promoters

Figures 2A, 2B:
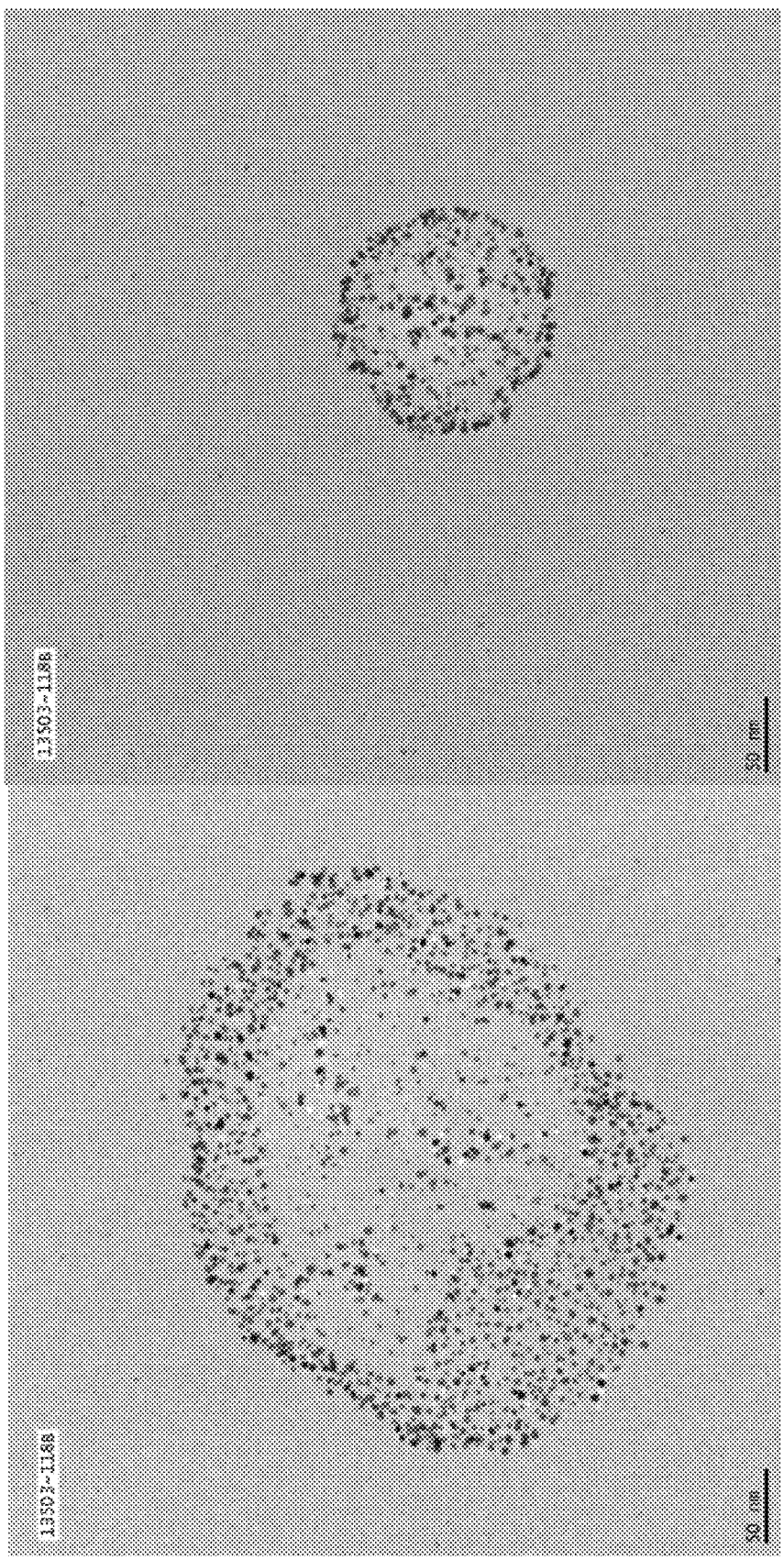
FIGS. 2A and 2B are additional images of clustered domain from the same experiment as FIGS. 1A and 1B, but at higher magnification. (bar=50 nm).

A filler-free test composition was prepared that was included a free radically polymerizable monomer, a free radical initiator, and a palladium salt of the invention. The purpose of this model composition was to determine the fate of the palladium salt via transmission electron microscopy following a typical adhesive cure profile. The test resin composition used to prepare these images included 94.5% PEAM 1044 (U.S. Pat. No. 7,285,613 B2, Example 3), 0.5% of the compound S-1, and 5.0% dicumyl peroxide. The mixture was cured under nitrogen in an oven that was ramped from room temperature to 175° C. followed by a fifteen-minute soak at 175° C. The cure of this test mixture was found to result in the development of clusters of nano disperse elemental palladium particles, which are indicated by the arrows in FIGS. 1A and 1B by TEM microscopy. FIGS. 2A and 2B show the same clusters at higher magnification. The TEM micrographs of FIGS. 2A and 2B show both disperse Pd particles in the field of view in addition to the Pd particle clusters. FIG. 3 shows disperse nano palladium particles in the cured resin matrix. It is clear from the TEM micrographs that the dispersed palladium particles are a few nanometers in size. The clusters of Pd particles evident in the TEM micrographs from FIGS. 1A, 1B, 2A and 2B are themselves composed of numerous nanometer-sized Pd particles. The dimensions of the particle clusters as shown in the TEM micrograph were still less than a micrometer across (approximately 0.4 μm). The identity of these particles and particle clusters were confirmed to be elemental palladium via EDX analysis (Energy Dispersive X-Ray analysis).

It is not clear why both nano-disperse Pd particles and nano Pd particle clusters were observed in the cured matrix of this experiment. It is possible that, due to differences in free radical monomer reactivity ratios, the polymerization of the base resin with compound S-1 resulted in both co-polymerized and homo-polymerized regions within the cured matrix. The thermal decomposition of these co-polymerized and homo-polymerized regions containing compound S-1 could thus result in a combination of nano-disperse and clustered nano Pd particles, respectively. Although it is believed that homogeneously distributed, nano-disperse Pd particles provide the maximal reduction of electrical resistance in silver-filled thermoset adhesives, clusters of Pd nano particles are also likely to facilitate improved electrical performance.

These results compare favorably to those previously reported e.g. for conductive silver particle containing films (see e.g. Southward et al., (1998) Polymer Preprints 39:423-4). It should be noted, however, that the test resin/conductivity promoter of this exemplary invention conductivity promoter required only a temperature of 175° C. for formation of nano disperse particles, while particles of similar appearance in Southward et al. required temperatures of 300° C., (see, for example, FIG. 5) a temperature incompatibly high for electronic applications.

What is claimed is:

1. A soluble conductivity promoter comprising a metal salt, the metal salt consists of
   a) a hydrocarbon moiety, and
   b) a metal ion,
   wherein the hydrocarbon moiety comprises an organic acid ligand which further includes a functionality selected from the group consisting of acrylate, methacrylate, acrylamide, methacrylamide, maleate, fumarate, citraconate, itaconate, itaconimide, citraconimide, vinyl ester, allyl ester, diallyl ester, triallyl ester, allyl amide, diallyl amide, thiol, phenol and oxetane functionalities.

2. The soluble conductivity promoter of claim 1, wherein the organic acid ligand comprises between five carbons and about 10 carbon atoms.

3. The soluble conductivity promoter of claim 1, wherein the hydrocarbon moiety comprises at least one branch in the hydrocarbon backbone.

4. The soluble conductivity promoter of claim 3, wherein the hydrocarbon moiety is a branched aliphatic acid.

5. The soluble conductivity promoter of claim 1, wherein the metal salt is a liquid at room temperature.

6. The soluble conductivity promoter of claim 1, wherein the metal salt decomposes at a temperature less than about 220° C.

7. The soluble conductivity promoter of claim 1, wherein the metal salt decomposes at a temperature less than about 200° C.

8. The soluble conductivity promoter of claim 1, wherein the metal ion is selected from the group consisting of Ag, Pd, Ni, Pt, and Au.

9. The soluble conductivity promoter of claim 8, wherein the metal ion is Pd.

10. The soluble conductivity promoter of claim 1 comprising at least one metal salt selected from the group consisting of:

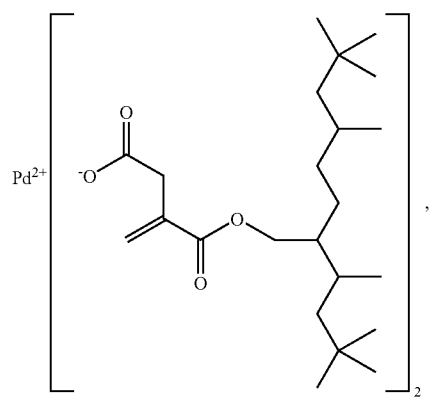

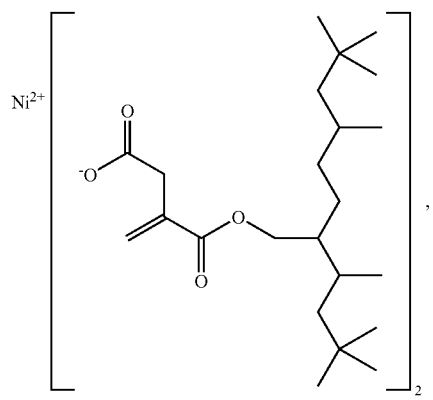

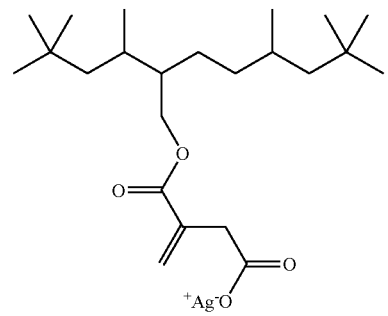

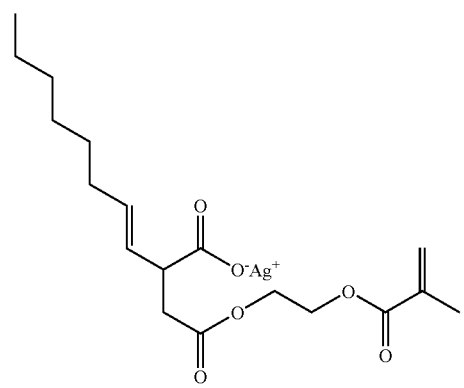

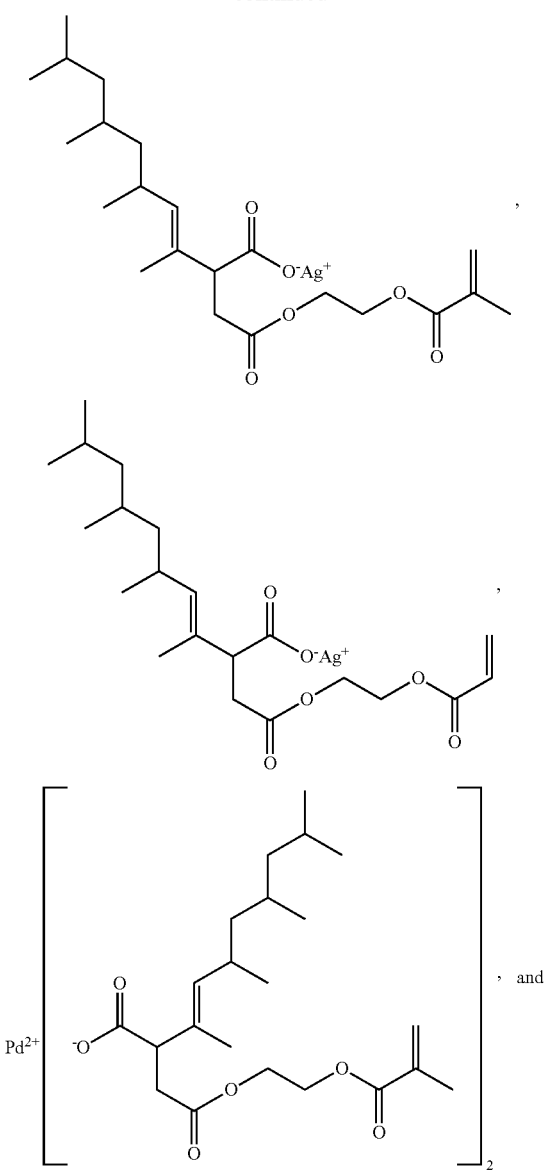

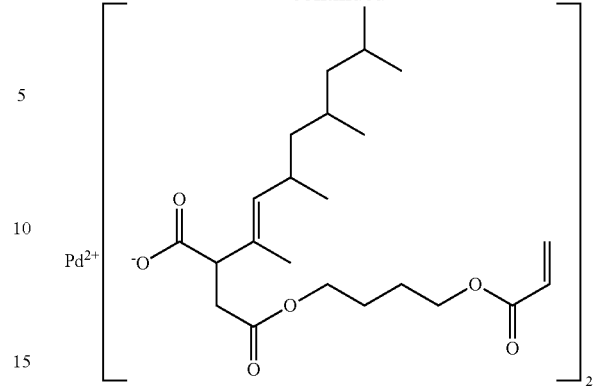

11. A method for preparing a soluble conductivity promoter of claim 1, comprising reacting a cyclic anhydride with an alcohol to generate an acid-ester and combining the acid-ester with a metal to form the soluble conductivity promoter.

12. A method for preparing the soluble conductivity promoter of claim 1, comprising reacting a cyclic anhydride with an amine to generate an acid-amide and combining the acid-amide with a metal to form the soluble conductivity promoter.

13. A method of increasing the conductivity of a thermoset resin comprising:
   a) incorporating a soluble conductivity promoter of claim 1 into the resin; and
   b) heating the resin, wherein the conductivity promoter decomposes to generate at least one free metal.

14. The method of claim 13, wherein nano-disperse metal domains are formed within the thermoset resin during step b.

15. An adhesive composition comprising:
   a) a silver flake filled adhesive, and
   b) a conductivity promoter according to claim 1,
   wherein the silver flake filled adhesive comprises an organic component and a silver flake component.

16. The adhesive composition of claim 15, wherein the organic component comprises about 15% of the total adhesive composition and the conductivity promoter is present at about 0.05% to about 1% of the total weight of the organic component.

17. The adhesive composition of claim 16, wherein the conductivity promoter is present at about 0.6% to about 0.8% of the total weight of the organic component.

* * * * *

UNITED STATES PATENT AND TRADEMARK OFFICE
CERTIFICATE OF CORRECTION

PATENT NO. : 8,398,898 B2  Page 1 of 1
APPLICATION NO. : 12/391204
DATED : March 19, 2013
INVENTOR(S) : Dershem It is certified that error appears in the above-identified patent and that said Letters Patent is hereby corrected as shown below:

In the Specification

Column 6, line 47, delete "–S(O)$_2$" and insert -- –S(O)$_2$– --;

Column 6, line 48, delete "–NR-C(O)" and insert -- –NR-C(O)– --;

Column 6, line 48, delete "–NR-C(O)-NR" and insert -- –NR-C(O)-NR– --;

Column 6, spanning lines 48-49, delete "–OC(O)-NR" and insert -- –OC(O)-NR– --.

Signed and Sealed this
Third Day of September, 2013

Teresa Stanek Rea
*Acting Director of the United States Patent and Trademark Office*